US011865361B2

(12) United States Patent
Perez et al.

(10) Patent No.: US 11,865,361 B2
(45) Date of Patent: Jan. 9, 2024

(54) SYSTEM AND METHOD FOR SCANNING PATTERN OPTIMIZATION FOR FLASH THERAPY TREATMENT PLANNING

(71) Applicants: Varian Medical Systems, Inc., Palo Alto, CA (US); Varian Medical Systems Particle Therapy GmBH, Troisdorf (DE); Varian Medical Systems International AG., Cham (CH)

(72) Inventors: Jessica Perez, Geneva (CH); Eric Abel, San Jose, CA (US); Michael Folkerts, Carrollton, TX (US); Christel Smith, Santa Barbara, CA (US); Adam Harrington, Glastonbury, CT (US); Timo Koponen, Espoo (FI); Reynald Vanderstraeten, Uccle (BE); Anthony Magliari, Newark, IL (US); Michiko Rossi, Espoo (FI)

(73) Assignees: VARIAN MEDICAL SYSTEMS, INC., Palo Alto, CA (US); VARIAN MEDICAL SYSTEMS PARTICLE THERAPY GMBH & CO. KG, Troisdorf (DE); SIEMENS HEALTHINEERS INTERNATIONAL AG, Cham (CH)

( * ) Notice: Subject to any disclaimer, the term of this patent is extended or adjusted under 35 U.S.C. 154(b) by 243 days.

(21) Appl. No.: 16/840,115

(22) Filed: Apr. 3, 2020

(65) Prior Publication Data

US 2021/0308486 A1    Oct. 7, 2021

(51) Int. Cl.
*A61N 5/10* (2006.01)

(52) U.S. Cl.
CPC ............ *A61N 5/1031* (2013.01); *A61N 5/10* (2013.01); *A61N 5/1007* (2013.01); *A61N 2005/1012* (2013.01); *A61N 2005/1087* (2013.01)

(58) Field of Classification Search
CPC ................... A61N 5/1031; A61N 5/10; A61N 2005/1087; A61N 5/1043
(Continued)

(56) References Cited

U.S. PATENT DOCUMENTS

| 4,163,901 A | 8/1979 | Azam |
| 4,914,681 A | 4/1990 | Klingenbeck et al. |

(Continued)

FOREIGN PATENT DOCUMENTS

| CN | 104001270 | 8/2014 |
| CN | 106730407 | 5/2017 |

(Continued)

OTHER PUBLICATIONS

Patriarca, Annalisa, et al. "Experimental set-up for FLASH proton irradiation of small animals using a clinical system." International Journal of Radiation Oncology* Biology* Physics 102.3 (2018): 619-626 (Year: 2018).*

(Continued)

*Primary Examiner* — Michael Maskell
(74) *Attorney, Agent, or Firm* — Harness, Dickey & Pierce, P.L.C.

(57) ABSTRACT

Embodiments of the present invention provide methods and systems for proton therapy planning that maximize the dose rate for different target sizes for FLASH therapy treatment are disclosed herein according to embodiments of the present invention. According to embodiments, non-standard scanning patterns can be generated, for example, using a TPS optimizer, to maximize dose rate and the overall (Continued)

FLASH effect for specific volumes at risk. The novel scanning patterns can include scanning subfields of a field that are scanned independently or spiral-shaped patterns, for example. In general, spot locations and beam paths between spots are optimized to substantially achieve a desired dose rate in defined regions of the patient's body for FLASH therapy treatment.

19 Claims, 10 Drawing Sheets

(58) Field of Classification Search
USPC .......................................... 250/492.1–493.1
See application file for complete search history.

(56) References Cited

U.S. PATENT DOCUMENTS

| | | | |
|---|---|---|---|
| 5,153,900 A | 10/1992 | Nomikos et al. | |
| 5,267,294 A | 11/1993 | Kuroda | |
| 5,550,378 A | 8/1996 | Skillicorn et al. | |
| 5,610,967 A | 3/1997 | Moorman et al. | |
| 5,625,663 A | 4/1997 | Swerdloff et al. | |
| 5,682,412 A | 10/1997 | Skillicom et al. | |
| 5,757,885 A | 5/1998 | Yao et al. | |
| 6,198,802 B1 | 3/2001 | Elliott et al. | |
| 6,222,544 B1 | 4/2001 | Tarr et al. | |
| 6,234,671 B1 | 5/2001 | Solomon et al. | |
| 6,260,005 B1 | 7/2001 | Yang et al. | |
| 6,379,380 B1 | 4/2002 | Satz | |
| 6,411,675 B1 | 6/2002 | Llacer | |
| 6,445,766 B1 | 9/2002 | Whitham | |
| 6,504,899 B2 | 1/2003 | Pugachev et al. | |
| 6,580,940 B2 | 6/2003 | Gutman | |
| 6,993,112 B2 | 1/2006 | Hesse | |
| 7,268,358 B2 | 9/2007 | Ma et al. | |
| 7,453,983 B2 | 11/2008 | Schildkraut et al. | |
| 7,515,681 B2 | 4/2009 | Ebstein | |
| 7,522,706 B2 | 4/2009 | Lu et al. | |
| 7,560,715 B2 | 7/2009 | Pedroni | |
| 7,590,219 B2 | 9/2009 | Maurer, Jr. et al. | |
| 7,616,735 B2 | 11/2009 | Maciunas et al. | |
| 7,623,623 B2 | 11/2009 | Raanes et al. | |
| 7,778,691 B2 | 8/2010 | Zhang et al. | |
| 7,807,982 B2 | 10/2010 | Nishiuchi et al. | |
| 7,831,289 B2 | 11/2010 | Riker et al. | |
| 7,835,492 B1 | 11/2010 | Sahadevan | |
| 7,907,699 B2 | 3/2011 | Long et al. | |
| 8,284,898 B2 | 10/2012 | Ho et al. | |
| 8,306,184 B2 | 11/2012 | Chang et al. | |
| 8,401,148 B2 | 3/2013 | Lu et al. | |
| 8,406,844 B2 | 3/2013 | Ruchala et al. | |
| 8,559,596 B2 | 10/2013 | Thomson et al. | |
| 8,600,003 B2 | 12/2013 | Zhou et al. | |
| 8,613,694 B2 | 12/2013 | Walsh | |
| 8,636,636 B2 | 1/2014 | Shukla et al. | |
| 8,644,571 B1 | 2/2014 | Schulte et al. | |
| 8,716,663 B2 | 5/2014 | Brusasco et al. | |
| 8,836,332 B2 | 9/2014 | Shvartsman et al. | |
| 8,847,179 B2 * | 9/2014 | Fujitaka | A61N 5/1036 250/492.1 |
| 8,903,471 B2 | 12/2014 | Heid | |
| 8,917,813 B2 | 12/2014 | Maurer, Jr. | |
| 8,948,341 B2 | 2/2015 | Beckman | |
| 8,958,864 B2 | 2/2015 | Amies et al. | |
| 8,983,573 B2 | 3/2015 | Carlone et al. | |
| 8,986,186 B2 | 3/2015 | Zhang et al. | |
| 8,992,404 B2 | 3/2015 | Graf et al. | |
| 8,995,608 B2 | 3/2015 | Zhou et al. | |
| 9,018,603 B2 | 4/2015 | Loo et al. | |
| 9,033,859 B2 | 5/2015 | Fieres et al. | |
| 9,079,027 B2 | 7/2015 | Agano et al. | |
| 9,149,656 B2 | 10/2015 | Tanabe | |
| 9,155,908 B2 | 10/2015 | Meltsner et al. | |
| 9,233,260 B2 | 1/2016 | Slatkin et al. | |
| 9,258,876 B2 | 2/2016 | Cheung et al. | |
| 9,283,406 B2 | 3/2016 | Prieels | |
| 9,308,391 B2 | 4/2016 | Liu et al. | |
| 9,330,879 B2 | 5/2016 | Lewellen et al. | |
| 9,333,374 B2 | 5/2016 | Iwata | |
| 9,468,777 B2 | 10/2016 | Fallone et al. | |
| 9,517,358 B2 | 12/2016 | Velthuis et al. | |
| 9,526,918 B2 | 12/2016 | Kruip | |
| 9,545,444 B2 | 1/2017 | Strober et al. | |
| 9,583,302 B2 | 2/2017 | Figueroa Saavedra et al. | |
| 9,636,381 B2 | 5/2017 | Basile | |
| 9,636,525 B1 | 5/2017 | Sahadevan | |
| 9,649,298 B2 | 5/2017 | Djonov et al. | |
| 9,656,098 B2 | 5/2017 | Goer | |
| 9,694,204 B2 | 7/2017 | Hardemark | |
| 9,776,017 B2 | 10/2017 | Flynn et al. | |
| 9,786,054 B2 | 10/2017 | Taguchi et al. | |
| 9,786,093 B2 | 10/2017 | Svensson | |
| 9,786,465 B2 | 10/2017 | Li et al. | |
| 9,795,806 B2 | 10/2017 | Matsuzaki et al. | |
| 9,801,594 B2 | 10/2017 | Boyd et al. | |
| 9,844,358 B2 | 12/2017 | Wiggers et al. | |
| 9,854,662 B2 | 12/2017 | Mishin | |
| 9,884,206 B2 | 2/2018 | Schulte et al. | |
| 9,931,522 B2 | 4/2018 | Bharadwaj et al. | |
| 9,962,562 B2 | 5/2018 | Fahrig et al. | |
| 9,974,977 B2 | 5/2018 | Lachaine et al. | |
| 9,987,502 B1 | 6/2018 | Gattiker et al. | |
| 10,007,961 B2 | 6/2018 | Grudzinski et al. | |
| 10,022,564 B2 | 7/2018 | Thieme et al. | |
| 10,071,264 B2 | 9/2018 | Liger | |
| 10,080,912 B2 | 9/2018 | Kwak et al. | |
| 10,092,774 B1 | 10/2018 | Vanderstraten et al. | |
| 10,183,179 B1 | 1/2019 | Smith et al. | |
| 10,188,875 B2 | 1/2019 | Kwak et al. | |
| 10,206,871 B2 | 2/2019 | Lin et al. | |
| 10,212,800 B2 | 2/2019 | Agustsson et al. | |
| 10,232,193 B2 | 3/2019 | Iseki | |
| 10,258,810 B2 | 4/2019 | Zwart et al. | |
| 10,272,264 B2 | 4/2019 | Ollila et al. | |
| 10,279,196 B2 | 5/2019 | West et al. | |
| 10,293,184 B2 | 5/2019 | Pishdad et al. | |
| 10,307,614 B2 | 6/2019 | Schnarr | |
| 10,307,615 B2 | 6/2019 | Ollila et al. | |
| 10,315,047 B2 | 6/2019 | Glimelius et al. | |
| 10,413,755 B1 | 9/2019 | Sahadevan | |
| 10,449,389 B2 | 10/2019 | Ollila et al. | |
| 10,485,988 B2 | 11/2019 | Kuusela et al. | |
| 10,525,285 B1 | 1/2020 | Friedman | |
| 10,549,117 B2 | 2/2020 | Vanderstraten et al. | |
| 10,603,514 B2 | 3/2020 | Grittani et al. | |
| 10,609,806 B2 | 3/2020 | Roecken et al. | |
| 10,636,609 B1 | 4/2020 | Bertsche et al. | |
| 10,660,588 B2 | 5/2020 | Boyd et al. | |
| 10,661,100 B2 | 5/2020 | Shen | |
| 10,682,528 B2 | 6/2020 | Ansorge et al. | |
| 10,702,716 B2 | 7/2020 | Heese | |
| 10,758,746 B2 | 9/2020 | Kwak et al. | |
| 10,870,018 B2 | 12/2020 | Bartkoski et al. | |
| 2007/0287878 A1 | 12/2007 | Fantini et al. | |
| 2008/0023644 A1 | 1/2008 | Pedroni | |
| 2009/0052623 A1 * | 2/2009 | Tome | A61B 5/6831 378/65 |
| 2009/0063110 A1 | 3/2009 | Failla et al. | |
| 2009/0287467 A1 | 11/2009 | Sparks et al. | |
| 2010/0072389 A1 | 3/2010 | Tachikawa et al. | |
| 2010/0119032 A1 | 5/2010 | Yan et al. | |
| 2010/0177870 A1 | 7/2010 | Nord et al. | |
| 2010/0178245 A1 | 7/2010 | Arnsdorf et al. | |
| 2010/0260317 A1 | 10/2010 | Chang et al. | |
| 2011/0006224 A1 | 1/2011 | Maltz et al. | |
| 2011/0091015 A1 | 4/2011 | Yu et al. | |
| 2011/0135058 A1 | 6/2011 | Sgouros et al. | |
| 2011/0280372 A1 | 11/2011 | Ivanov | |
| 2012/0076271 A1 | 3/2012 | Yan et al. | |
| 2012/0157746 A1 | 6/2012 | Meltsner et al. | |
| 2012/0171745 A1 | 7/2012 | Itoh | |
| 2012/0197058 A1 | 8/2012 | Shukla et al. | |
| 2013/0116929 A1 | 5/2013 | Carlton et al. | |

(56) References Cited

U.S. PATENT DOCUMENTS

| | | |
|---|---|---|
| 2013/0150922 A1 | 6/2013 | Butson et al. |
| 2013/0177641 A1 | 7/2013 | Ghoroghchian |
| 2013/0231516 A1 | 9/2013 | Loo et al. |
| 2014/0177807 A1 | 6/2014 | Lewellen et al. |
| 2014/0185776 A1 | 7/2014 | Li et al. |
| 2014/0206926 A1 | 7/2014 | van der Laarse |
| 2014/0275706 A1 | 9/2014 | Dean et al. |
| 2014/0369476 A1 | 12/2014 | Harding |
| 2015/0011817 A1 | 1/2015 | Feng |
| 2015/0202462 A1 | 7/2015 | Iwata |
| 2015/0202464 A1 | 7/2015 | Brand et al. |
| 2015/0306423 A1 | 10/2015 | Bharat et al. |
| 2016/0279444 A1 | 9/2016 | Schlosser |
| 2016/0310764 A1 | 10/2016 | Bharadwaj et al. |
| 2017/0189721 A1 | 7/2017 | Sumanaweera et al. |
| 2017/0203129 A1 | 7/2017 | Dessy |
| 2017/0281973 A1 | 10/2017 | Allen et al. |
| 2018/0021594 A1 | 1/2018 | Papp et al. |
| 2018/0043183 A1 | 2/2018 | Sheng et al. |
| 2018/0056090 A1 | 3/2018 | Jordan et al. |
| 2018/0099154 A1 | 4/2018 | Prieels |
| 2018/0099155 A1 | 4/2018 | Prieels et al. |
| 2018/0099159 A1 | 4/2018 | Forton et al. |
| 2018/0154183 A1 | 6/2018 | Sahadevan |
| 2018/0197303 A1 | 7/2018 | Jordan et al. |
| 2018/0207425 A1 | 7/2018 | Carlton et al. |
| 2018/0236268 A1 | 8/2018 | Zwart et al. |
| 2019/0022407 A1 | 1/2019 | Abel et al. |
| 2019/0022422 A1 | 1/2019 | Trail et al. |
| 2019/0054315 A1 | 2/2019 | Isola et al. |
| 2019/0070435 A1 | 3/2019 | Joe Anto et al. |
| 2019/0168027 A1 | 6/2019 | Smith et al. |
| 2019/0255361 A1 | 8/2019 | Mansfield |
| 2019/0299027 A1 | 10/2019 | Fujii et al. |
| 2019/0299029 A1 | 10/2019 | Inoue |
| 2019/0351259 A1 | 11/2019 | Lee et al. |
| 2020/0001118 A1 | 1/2020 | Snider, III et al. |
| 2020/0009405 A1* | 1/2020 | Kontaxis ............. A61N 5/1067 |
| 2020/0022248 A1 | 1/2020 | Yi et al. |
| 2020/0030633 A1 | 1/2020 | Van Heteren et al. |
| 2020/0035438 A1 | 1/2020 | Star-Lack et al. |
| 2020/0069818 A1 | 3/2020 | Jaskula-Ranga et al. |
| 2020/0164224 A1 | 5/2020 | Vanderstraten et al. |
| 2020/0178890 A1 | 6/2020 | Otto |
| 2020/0197730 A1 | 6/2020 | Safavi-Naeini et al. |
| 2020/0254279 A1 | 8/2020 | Ohishi |
| 2020/0269068 A1 | 8/2020 | Abel et al. |
| 2020/0276456 A1* | 9/2020 | Swerdloff ............ A61N 5/1049 |
| 2020/0282234 A1 | 9/2020 | Folkerts et al. |

FOREIGN PATENT DOCUMENTS

| | | |
|---|---|---|
| CN | 107362464 | 11/2017 |
| CN | 109966662 | 7/2019 |
| CN | 111481840 | 8/2020 |
| CN | 111481841 | 8/2020 |
| EA | 010207 | 6/2008 |
| EP | 0979656 | 2/2000 |
| EP | 2851104 | 3/2015 |
| EP | 3338858 | 6/2018 |
| EP | 3384961 | 10/2018 |
| EP | 3421087 | 1/2019 |
| EP | 3453427 | 3/2019 |
| EP | 3586920 | 1/2020 |
| JP | 2617283 | 6/1997 |
| JP | 2019097969 | 6/2019 |
| WO | 2007017177 | 2/2007 |
| WO | 2010018476 | 2/2010 |
| WO | 2013081218 | 6/2013 |
| WO | 2013133936 | 9/2013 |
| WO | 2014139493 | 9/2014 |
| WO | 2015038832 | 3/2015 |
| WO | 2015102680 | 7/2015 |
| WO | 2016122957 | 8/2016 |
| WO | 2017156316 | 9/2017 |
| WO | 2017174643 | 10/2017 |
| WO | 2018137772 | 8/2018 |
| WO | 2018152302 | 8/2018 |
| WO | 2019097250 | 5/2019 |
| WO | 2019103983 | 5/2019 |
| WO | 2019164835 | 8/2019 |
| WO | 2019166702 | 9/2019 |
| WO | 2019185378 | 10/2019 |
| WO | 2019222436 | 11/2019 |
| WO | 2020018904 | 1/2020 |
| WO | 2020064832 | 4/2020 |
| WO | 2020107121 | 6/2020 |
| WO | 2020159360 | 8/2020 |

OTHER PUBLICATIONS

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/s41598-020-65819-y.

Ibrahim Oraiqat et al., "An Ionizing Radiation Acoustic Imaging (iRAI) Technique for Real-Time Dosimetric Measurements for FLASH Radiotherapy," Medical Physics, vol. 47, Issue 10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5lbHNldmllci5jb20vY29udGVudC9hcnRpY2xlL3BpaS9zMDE2NzgxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/ doi: 10.1118/1.4761951.

Favaudon et al., "Ultrahigh dose-rate, "flash" irradiation minimizes the side-effects of radiotherapy," Cancer / Radiotherapy, vol. 19, Issues 6-7, Oct. 2015, pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181(2): 177-183. Published Feb. 13, 2014, DOI: http://dx.doi.org/10.1667/RR13464.1.

Bjorn Zackrisson, "Biological Effects Of High Energy Radiation And Ultra High Dose Rates," Umea University Medical Dissertations, New series No. 315-ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

Bw Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic

(56) References Cited

OTHER PUBLICATIONS models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated radiation therapy," Int. J. Radiation Oncology Biol. Phys., vol. 51, Issue 5, p. 1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

A. J. Lomax et al, "Intensity modulated proton therapy: A clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for early and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013- eng.pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.

J. Groen, "FLASH optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019 https://www.ncbi.nlm.nih.gov/pmc/articles/PMC5904040/ Published in final edited form as: Med Phys. Apr. 2018; 45(4): 1338-1350. Published online Mar. 1, 2018. doi: 10.1002/mp.12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by

(56) References Cited

OTHER PUBLICATIONS

Real-Time Imaging and Gating and Reduces Equipment Size," Plos One, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "FLASH radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.

Mevion Medical Systems, "Focus On The Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of FLASH Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/ Published in final edited form as: Radiat Res. Jan. 2020; 193(1): 1-4. Published online Oct. 28, 2019. doi: 10.1667/RR15537.1.

Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

"FlashRad: Ultra-high dose-rate FLASH radiotherapy to minimize the complications of radiotherapy," 2014, https://siric.curie.fr/sites/default/files/atoms/files/flashrad.pdf.

Tami Freeman, "FLASH radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

Intraop Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A FLASH back to radiotherapy's past and then fast forward to the future," J Cancer Prev Curr Res. 2019; 10(6):142-144. published Nov. 13, 2019, DOI: 10.15406/jcpcr.2019.10.00407.

P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: FLASH: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp.13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/ Published in final edited form as: Radiother Oncol. Oct. 2019; 139: 51-55. Published online Mar. 5, 2019. doi: 10.1016/j.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement, S164-S165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394/.

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.

Oncolink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for-me.

Marco Durante et al., "Faster and safer? FLASH ultra-high dose rate in radiotherapy," Br J Radiol 2018; 91(1082): 20170628, British Institute of Radiology, Published Online: Dec. 15, 2017, https://doi.org/10.1259/bjr.20170628.

John R. Fischer, "PMB launches FLASH radiotherapy system for use in clinical trials," HealthCare Business News, Jun. 29, 2020, DOTmed.com, Inc., https://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6,

(56) References Cited

OTHER PUBLICATIONS 2018, https://clincancerres.aacrjournals.org/content/clincanres/early/2018/06/06/1078-0432.CCR-17-3375.full.pdf.

* cited by examiner

SYSTEM AND METHOD FOR SCANNING PATTERN OPTIMIZATION FOR FLASH THERAPY TREATMENT PLANNING

FIELD

Embodiments of the present invention relate generally to the field of radiotherapy treatment. More specifically, embodiments of the present invention relate to systems and methods for proton therapy treatment planning and generating scanning patterns.

BACKGROUND

Particle therapy using protons or other ions is a type of radiotherapy that uses an external beam to provide targeted ionizing radiation to a tumor. Protons or other positively charged ions are sent to an accelerator to bring the particles' energy to a predetermined value. The protons or other ions then move through a beam-transport system, where magnets are used to shape, focus and/or direct the proton or other ion beam as necessary.

Standard radiation therapy deposits energy in "spots" along the path of the beam to a target tumor. However, the reach of the energy also extends beyond the tissues of the target tumor, and may deliver radiation to healthy tissue around the tumor site. This excess radiation may damage normal tissue or organs near the target area. Moreover, the selection of specific energies and the number of spots is decided based only on patient geometry and hardware constraints. The subsequent optimization to achieve the dosimetric criteria for treatment is traditionally performed only on spot intensities, which can produce less than optimal results.

Radiation treatment plans can be optimized according to given dose volume constraints for target volume and organs at risk and according to plan robustness using commercially available treatment planning systems. Dose distributions are calculated using beam characteristics and a machine specific dose calibration. However, machine or system limitations can lead to translation of an aimed dose distribution into machine/treatment delivery system parameters that generate an unacceptable or suboptimal treatment plan. For example, the generated treatment plan may not use the full system/machine capability and thereby may not make use of the system in the most efficient and reliable manner. The treatment plan can be optimized for efficiency using a trial and error methodology involving modification of several complex associated plan parameters (e.g., energy layer distance, spot size or spot spacing) required for multi-directional optimization. Even if an optimized treatment plan finally passes the criteria for plan quality and treatment delivery time, the application at the machine may fail or may not achieve the optimal delivery efficiency as requested by plan objectives during treatment planning due to machine specific capability limitations of combined plan parameters which are not taken into account by currently available commercial treatment planning systems.

For example, in proton therapy treatment, a pencil beam is scanned across the target area to deliver the radiation dose. The scanning pattern goes line-by-line regardless of target shape or time to deliver the field. FLASH therapy delivers ultra-high dose rate treatment to a target and has been shown to reduce normal tissue toxicity in preclinical studies. Little is known as to the underlying biological mechanism behind the FLASH effect, but it is postulated to have increasing benefits with increasing dose rate. In pencil beam scanning (PBS), the dose rate becomes difficult to define since each voxel dose rate is influenced by its neighbors. A treatment planning system (TPS) is used to generate spots in a grid pattern and to determine the dose of the spots. This information is stored in a treatment plan that is executed by a proton therapy treatment system (e.g., a gantry) that delivers the dose using raster scanning.

Currently, the scanning pattern created by TPS is limited to line-by-line scanning, and is typically optimized to minimize the total dose received by the patient. Importantly, there is currently no way to change or customize that pattern to optimize FLASH dose rate delivery. Moreover, existing techniques for delivery of the dose use standard scanning patterns that do not take into account the dose rate, which can be problematic depending on the shape and size of the target. For example, for a relatively large target, scanning the target line-by-line may not be the most efficient means to deliver the dose and can actually decrease the applied dose rate dramatically. Therefore, standard scanning patterns are often limited to lower dose rate, especially in the context of PBS FLASH delivery. However, for high dosage rate treatments, such as PBS FLASH therapy, it is desirable to maximize the dose rate applied to normal tissue.

Therefore, an improved approach to FLASH treatment planning is needed that can maximize the dose rate for different target sizes, including relatively large targets, different shapes, and different locations.

SUMMARY

Accordingly, embodiments of the present invention include an improved approach to FLASH treatment planning that can maximize the dose rate for FLASH treatment. More specifically, methods and systems for proton therapy planning that maximize the dose rate for different target sizes, shapes, and/or locations for FLASH therapy treatment are disclosed herein according to embodiments of the present invention. According to embodiments, non-standard scanning patterns can be generated, for example, using a TPS optimizer, to maximize dose rate and the overall FLASH effect for specific volumes at risk. The novel scanning patterns can include scanning subfields of a field that are scanned independently or spiral-shaped patterns, for example. In general, spot locations and beam paths between spots are optimized to substantially achieve a desired dose rate in defined regions of the patient's body for FLASH therapy treatment.

According to one embodiment, a system for proton therapy treatment is disclosed. The system includes a gantry including a nozzle configured to emit a controllable proton beam, a proton therapy treatment system that controls the gantry according to a treatment plan, and a treatment planning system including a memory for storing image data and the treatment plan, and a processor operable to perform a method of generating the treatment plan. The method includes receiving imaging data of a target volume, dividing the imaging data of the target volumes into a scanning pattern including a plurality of subfields including a first scanning direction and a second scanning direction, optimizing the scanning pattern to achieve a desired dose rate, and outputting a treatment plan including the scanning pattern. The treatment plan is operable to instruct a proton therapy treatment system to perform proton therapy treatment on the target volume according to the scanning pattern, and the proton therapy treatment system, in accordance with the treatment plan, scans in the first scanning direction at a faster scanning rate and scans in the second scanning direction at a slower scanning rate. The treatment plan is a proton therapy treatment plan.

According to some embodiments, the method further includes performing proton therapy treatment using the proton therapy treatment system according to the optimized proton therapy treatment plan.

According to some embodiments, the method further includes receiving the desired dose rate as input.

According to some embodiments, the method further includes determining the desired dose rate according to machine parameters associated with the proton therapy treatment system.

According to some embodiments, the plurality of subfields is scanned independently by the proton therapy treatment system.

According to some embodiments, the dividing the imaging data of the target volume into a scanning pattern including a plurality of subfields is performed based on a size of the target volume.

According to some embodiments, the desired dose rate is a upper limit dose rate of the proton therapy treatment system.

According to another embodiment, a method of proton therapy treatment is disclosed. The method includes receiving imaging data of a target volume, dividing the imaging data of the target volume into a scanning pattern including a plurality of subfields, the plurality of subfields including a first scanning direction and a second scanning direction, optimizing the scanning pattern to achieve a desired dose rate, and outputting a proton therapy treatment plan including the scanning pattern, the proton therapy treatment plan is operable to instruct a proton therapy treatment system to perform proton therapy treatment according to the scanning pattern, and further the proton therapy treatment system is operable to scan in the first scanning direction at a faster scanning rate, and operable to scan in the second scanning direction at a slower scanning rate.

According to some embodiments, the method includes performing proton therapy treatment using the proton therapy treatment system according to the proton therapy treatment plan.

According to some embodiments, the method includes receiving the desired dose rate as input.

According to some embodiments, the method includes determining the desired dose rate according to machine parameters associated with the proton therapy treatment system.

According to some embodiments, the plurality of subfields is scanned independently by the proton therapy treatment system.

According to some embodiments, dividing the imaging data of the target volume into a scanning pattern including a plurality of subfields is performed based on at least one of: a size of the target volume; a shape of the target volume; and a location of the target volume.

According to some embodiments, the desired dose rate is an upper limit dose rate of the proton therapy system.

According to a different embodiment, a method for proton therapy treatment is disclosed. The method includes receiving imaging data of a target volume of a patient, determining a size of the target volume based on the imaging data, generating a scanning pattern based on the size of the target volume, optimizing the scanning pattern to reduce to a lower threshold limit an amount of radiation received by healthy tissue of the patient, the scanning pattern includes a substantially spiral-shaped scanning pattern, and outputting a proton therapy treatment plan including the scanning pattern, the proton therapy treatment plan is operable to instruct a proton therapy treatment system to perform proton therapy treatment according to the scanning pattern.

According to some embodiments, the method includes performing proton therapy treatment using the proton therapy treatment system according to the treatment plan.

According to some embodiments, the scanning pattern is aligned to a grid-shaped pattern.

According to some embodiments, the scanning pattern is not aligned to a grid-shaped pattern.

According to some embodiments, the proton therapy treatment plan includes performing FLASH proton therapy.

According to some embodiments, the proton therapy treatment system is configured for pencil beam scanning.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION

Figure 1:
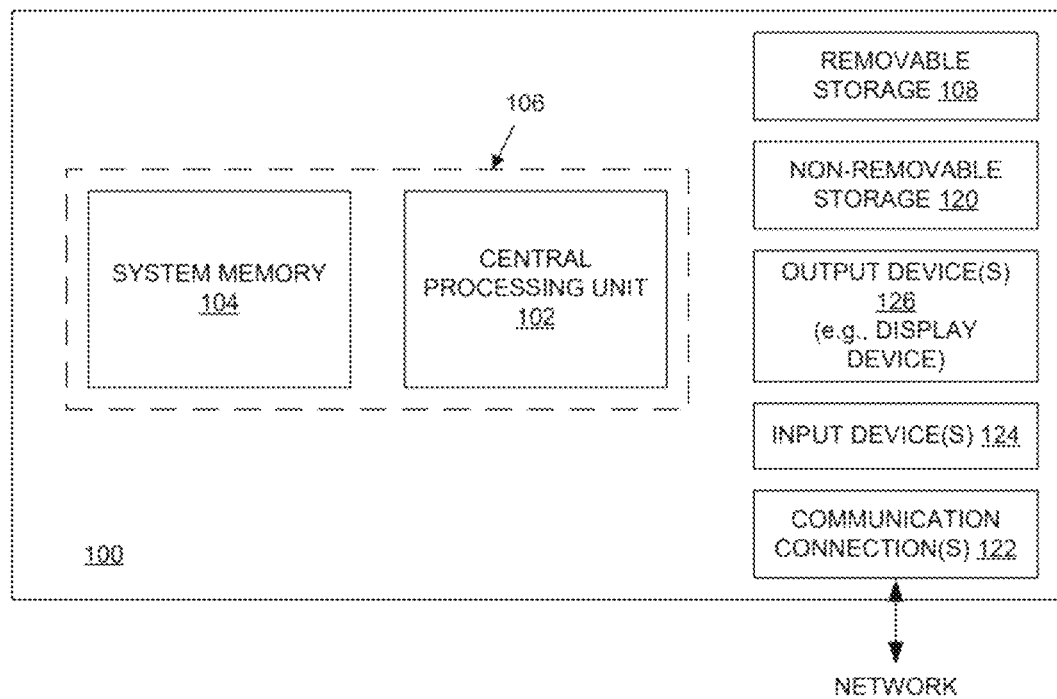
FIG. 1 shows a block diagram of an example of a computing system upon which the embodiments described herein may be implemented.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Portions of the detailed description that follows are presented and discussed in terms of a method or process. Although steps and sequencing thereof are disclosed in a figure herein describing the operations of this method, such steps and sequencing are exemplary. Embodiments are well suited to performing various other steps or variations of the steps recited in the flowchart (e.g., FIGS. 5A and 5B) of the figures herein, and in a sequence other than that depicted and described herein.

The portions of the detailed description that are presented in terms of procedures, steps, logic blocks, processing, and other symbolic representations are of operations on data bits that can be performed on computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "generating," "writing," "including," "storing," "transmitting," "traversing," "associating," "identifying," "optimizing" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Some embodiments may be described in the general context of computer-executable instructions, such as program modules or instructions, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

Novel Scanning Pattern Optimization for Flash Therapy Treatment

The following description is presented to enable a person skilled in the art to make and use the embodiments of this invention; it is presented in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present invention is not limited to the embodiments shown, but is to be accorded the widest scope consistent with the principles and features disclosed herein.

Methods and systems for proton therapy planning that maximize the dose rate for different target sizes, shapes, and locations for FLASH therapy treatment are disclosed herein according to embodiments of the present invention. According to embodiments, non-standard, novel scanning patterns can be generated, for example, using a TPS optimizer, to maximize dose rate and the overall FLASH effect for specific volumes at risk. The novel scanning patterns can include scanning subfields of a field that are scanned independently or may include spiral-shaped patterns to achieve a desired dose rate and/or to minimize radiation received by healthy tissue. In general, spot locations and beam paths between spots are optimized in accordance with embodiments of the present invention to substantially achieve a desired dose rate in defined regions of the patient's body for FLASH therapy treatment.

According to one embodiment, scanning pattern optimization is performed by a TPS to generate a proton therapy plan that causes a proton therapy system (e.g., a gantry) to scan a beam (e.g., a pencil beam) faster in one direction compared to another direction in order to increase or maximize the dose rate. By maximizing the dose rate, the dose accumulation time for healthy tissue is minimized. For example, for a relatively large target, sub-fields of the target can be divided into oblong rectangular subfields, and the treatment plan instructs the proton therapy system to scan the long dimension of a rectangle at a faster predefined scanning rate, and conversely, to scan the short dimension of the rectangular subfields at a slower predefined scanning rate. The overall size/area of a subfield (e.g., rectangle or rectangular subfield) can be determined based on the desired dose rate that the optimizer is attempting to achieve and/or a specified nozzle current, for example. According to some embodiments, the scanning pattern is optimized to increase or maximize the total biological FLASH effect applied by the proton therapy system.

According to another embodiment, scanning pattern optimization is performed by a TPS to generate a proton therapy plan that causes a proton therapy system (e.g., a gantry) to scan a beam (e.g., a pencil beam) in accordance with a scanning pattern that minimizes the number of scans that are performed by the proton therapy system that irradiate healthy tissue (e.g., healthy tissue voxels). Generally a voxel in the beam path will receive a full dose/dose rate, as well as some dose from the lateral penumbra of adjacent beams, and these "extra" doses do not necessarily produce a FLASH dose rate. Therefore, the scanning pattern optimization performed by the TPS attempts to minimize the "extra" dose from adjacent beams, which is especially critical in the context of FLASH therapy for ensuring that the majority of healthy tissue voxels only receive the healthy tissue dose rate specified by the treatment plan.

Some embodiments optimize a primary scanning axis angle to maximize dose rate by reducing the overall scanning time for a given target shape and/or orientation, for example, based on scanning magnet speed characteristics.

FIG. 1 shows a block diagram of an example of a computing system 100 upon which the embodiments described herein may be implemented. In a basic configuration, the system 100 includes at least one processing unit 102 and memory 104. This most basic configuration is illustrated in FIG. 1 by dashed line 106. The system 100 may also have additional optional features and/or functionality. For example, the system 100 may also include additional storage (removable and/or non-removable) including, but not limited to, solid state, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like. Depending on how it is to be used, the system 100—by executing the appropriate instructions or the like—can be used to implement a planning system used to generate a proton therapy plan that causes a proton therapy system (e.g., a gantry) to scan a beam (e.g., a pencil beam) faster in one direction compared to another direction in order to increase or maximize the dose rate. For example, for a relatively large target, sub-fields of the target can be divided into oblong rectangular subfields, and the treatment plan instructs the proton therapy system to scan the long dimension of a rectangle at a faster predefined scanning rate, and to scan the short dimension of the rectangles at a slower predefined scanning rate. The scanning pattern of the proton therapy plan can also be optimized to cause the proton therapy system to scan the beam in a scanning pattern that minimizes the amount of radiation received by healthy tissue. More generally, system 100 can be used to generate and/or optimize proton therapy treatment plans in accordance with the present invention.

Figure 2:
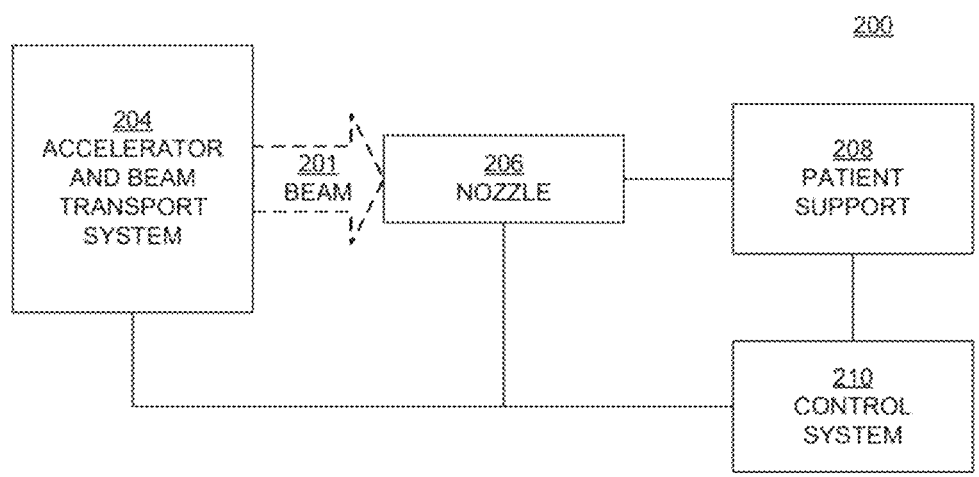
FIG. 2 is a block diagram showing selected components of a radiation treatment system upon which embodiments according to the present invention can be implemented.

FIG. 2 is a block diagram showing selected components of a radiation treatment system 200 upon which embodiments according to the present invention can be implemented. In the example of FIG. 2, the system 200 includes an accelerator and beam transport system 204 that is operable to generate and/or accelerate a beam 201. Embodiments according to the invention can generate and deliver beams of various types including, for instance, proton beams, electron beams, neutron beams, photon beams, ion beams, or atomic nuclei beams (e.g., using elements such as carbon, helium, or lithium). The operations and parameters of the accelerator and beam transport system 204 are controlled so that the intensity, energy, size, and/or shape of the beam are dynamically modulated or controlled during treatment of a patient according to an optimized radiation treatment plan produced by and stored within system 100 as discussed above.

A recent radiobiology study has demonstrated the effectiveness of delivering an entire, relatively high therapeutic radiation dose to a target within a single, short period of time. This type of treatment is referred to generally herein as FLASH radiation therapy (FLASH RT). Evidence to date suggests that FLASH RT advantageously spares normal, healthy tissue from damage when that tissue is exposed to only a single irradiation for only a very short period of time.

For FLASH RT, the accelerator and beam transport system 204 can generate beams that can deliver at least four (4) grays (Gy) in less than one second, and may deliver as much as 40 Gy or more in less than one second. The control system 210 can execute a treatment plan for FLASH RT, and the plan can be generated or optimized by system 100 executing an optimization algorithm or procedure in accordance with embodiments of the present invention.

The nozzle 206 is used to aim the beam toward various locations (e.g., of a target) within a patient supported on the patient support device 208 (e.g., a chair, couch, or table) in a treatment room. A target may be an organ, a portion of an organ (e.g., a volume or region within the organ), a tumor, diseased tissue, or a patient outline, for instance.

The nozzle 206 may be mounted on or may be a part of a gantry structure (FIG. 3) that can be moved relative to the patient support device 208, which may also be moveable. In embodiments, the accelerator and beam transport system 204 are also mounted on or are a part of the gantry structure; in another embodiment, the accelerator and beam transport system are separate from (but in communication with) the gantry structure.

The control system 210 of FIG. 2 receives and implements a prescribed treatment plan which is generated and/or optimized according to embodiments of the present invention. In embodiments, the control system 210 includes a computing system having a processor, memory, an input device (e.g., a keyboard), and optionally a display; the system 100 of FIG. 1 is an example of such a platform for the control system 210. The control system 210 can receive data regarding the operation of the system 200. The control system 210 can control parameters of the accelerator and beam transport system 204, nozzle 206, and patient support device 208, including parameters such as the energy, intensity, size, and/or shape of the beam, direction of the nozzle, and position of the patient support device (and the patient) relative to the nozzle, according to data the control system 210 receives and according to the radiation treatment plan.

Figure 3:
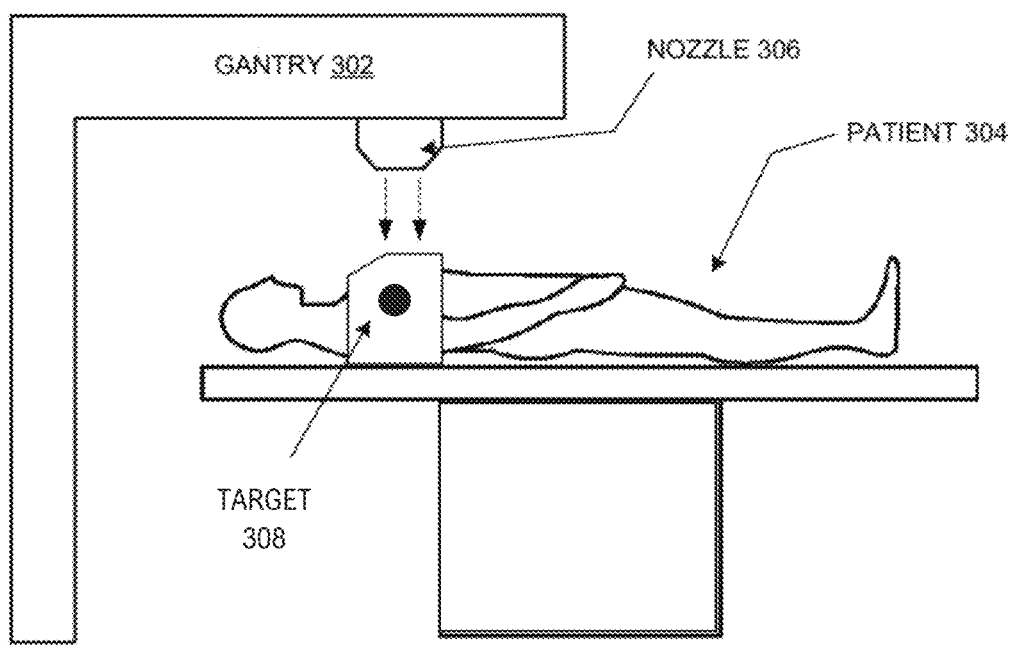
FIG. 3 illustrates elements of a radiation treatment system in accordance with embodiments of the present invention.

FIG. 3 illustrates elements of a radiation treatment system 300 for treating a patient 304 in accordance with embodiments of the present invention. The system 300 is an example of an implementation of the radiation treatment system 200 of FIG. 2, for example. In embodiments, the gantry 302 and nozzle 306 can be moved up and down the length of the patient 304 and/or around the patient, and the gantry and nozzle can move independently of one another. While the patient 304 is supine in the example of FIG. 3, the invention is not so limited. For example, the patient 304 can instead be seated in a chair or positioned in any orientation. The gantry 302 can be controlled by a treatment system using an optimized treatment plan generated according to embodiments of the present invention.

Figure 4:
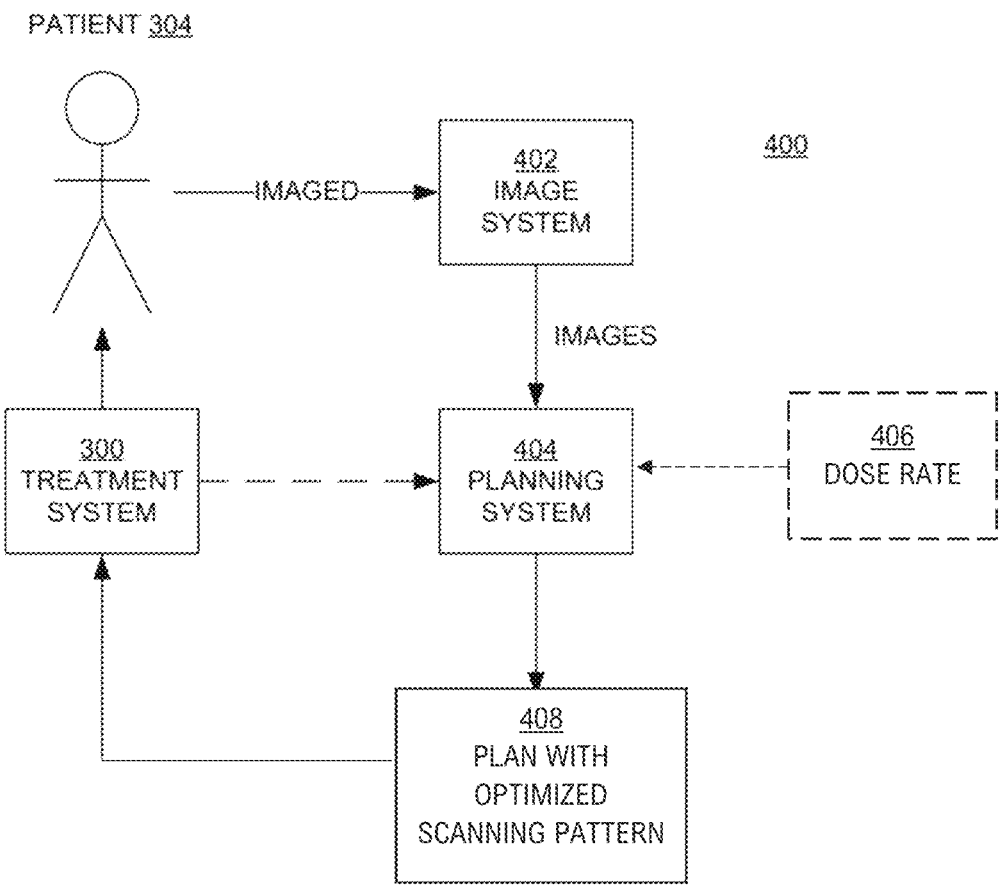
FIG. 4 is a block diagram illustrating components in a process for creating an optimized proton therapy treatment plan and scanning pattern in embodiments according to the present invention.

With regard to FIG. 4, an exemplary proton therapy system 400 for imaging and treating a patient 304 is depicted according to embodiments of the present invention. In the example of FIG. 4, patient 304 is imaged using an image system 402 that uses, for example, x-rays, magnetic resonance imaging (MM), and computed tomography (CT). When CT or MM imagery, for example, is used, a series of two-dimensional (2D) images are taken from a 3D volume and stored in memory. Each 2D image is an image of a cross-sectional "slice" of the 3D volume. The resulting collection of 2D cross-sectional slices can be combined to create a 3D model or reconstruction of the patient's anatomy (e.g., internal organs) and stored in memory. The 3D model will contain organs of interest, which may be referred to as structures of interest. Those organs of interest include the organ targeted for radiation therapy (a target), as well as other organs that may be at risk of radiation exposure during treatment. According to some embodiments, the imaging process is a separate process from the treatment planning process, and the treatment planning process can include receiving stored imaging data from a prior imaging session, for example.

One purpose of the 3D model is the preparation of a radiation treatment plan. To develop a patient-specific radiation treatment plan, information is extracted from the 3D model to determine parameters such as organ shape, organ volume, tumor shape, tumor location in the organ, and the position or orientation of several other structures of interest as they relate to the affected organ and any tumor. The radiation treatment plan can specify, for example, how many radiation beams to use and which angle from which each of the beams will be delivered.

In embodiments according to the present invention, the images from the image system 402 are input to a planning system 404. In embodiments, the planning system 404 includes a computing system having a processor, memory, an input device (e.g., a keyboard), and a display. The system 100 of FIG. 1 is an example of a platform for the planning system 404.

Continuing with reference to FIG. 4, the planning system 404 executes software that is capable of producing an optimized treatment plan for treating patient 304. The treatment planning system 404 can receive imagery data generated by image system 402 to implement a planning system used to generate a proton therapy plan that causes the proton therapy system 300 to scan a beam faster in one direction compared to another direction in order to increase or maximize the dose rate, or to achieve a prescribed dose rate 406 which can be optionally received as input by the planning system 404. For example, for a relatively large target, sub-fields of the target can be divided into oblong rectangular subfields, and the treatment plan 408 instructs the proton therapy system to scan the long dimension of a rectangle at a faster predefined scanning rate, and conversely, to scan the short dimension of the rectangles at a slower predefined scanning rate.

The scanning pattern of the proton therapy plan 408 can also be optimized to cause the proton therapy system 300 to scan the beam in a scanning pattern that minimizes the amount of radiation received by healthy tissue. More generally, planning system 404 can be used to generate and/or optimize proton therapy treatment plans in accordance with the present invention. The treatment planning system 404 outputs an optimized plan 408 according to an optimizing algorithm. The optimized plan 408 is then used to configure treatment system 300 for performing proton therapy treatment on patient 304 using gantry 302, for example.

Figure 5A:
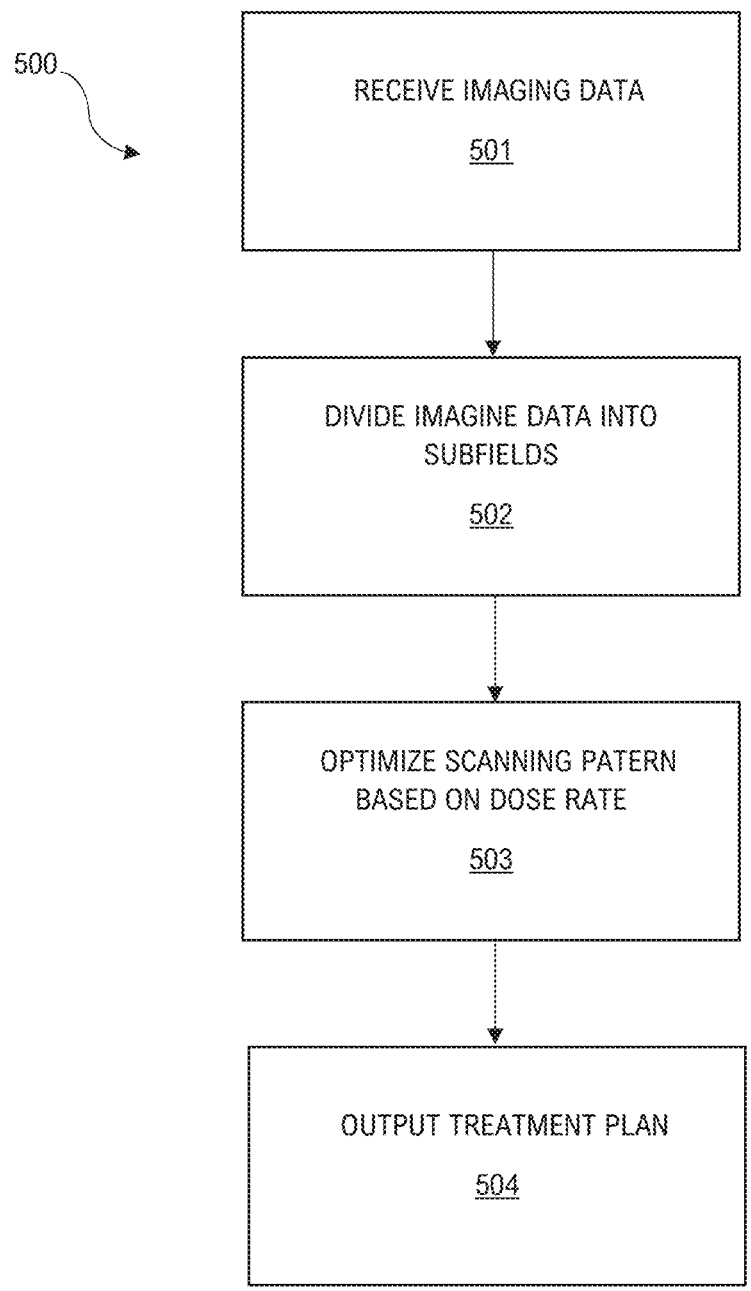
FIG. 5A is a flow-chart depicting an exemplary sequence of computer controlled steps for automatically creating an optimized proton therapy treatment plan and scanning pattern to optimize dose rate according to embodiments of the present invention.

With regard to FIG. 5A, an exemplary sequence of computer implemented steps 500 for automatically generating a proton therapy treatment plan is depicted according to embodiments of the present invention. The procedure 500 produces a proton treatment plan that is optimized to increase or maximize a dose rate applied by a proton therapy treatment system to normal/healthy tissue while maximizing dose received by the target volume and minimizing the dose received by normal tissue.

At step 501, imaging data of a target volume is received. The image data can originate from computer memory or from a scan of a target volume of a patient.

At step 502, imaging data of the target volumes is divided into a scanning pattern including a plurality of subfields. The subfields include a first scanning direction and a second scanning direction.

At step 503, the scanning pattern is optimized to achieve a desired dose rate.

At step 504, a proton therapy treatment plan is output including the scanning pattern including a scanning methodology. The proton therapy treatment plan is operable to instruct a proton therapy treatment system to perform proton therapy treatment according to the scanning pattern. The proton therapy treatment system scans in accordance with the scanning methodology in which scanning in the first scanning direction is performed at a faster scanning rate, and conversely, scanning in the second scanning direction is performed at a slower scanning rate.

According to some embodiments, a custom dose rate is received as user input and is used as the desired dose rate.

According to some embodiments, the desired dose rate is based on the maximum dose rate that can be produced by the proton therapy system. The maximum dose rate and desired dose rate can be determined according to machine parameters associated with the proton therapy treatment system, for example. According to some embodiments, the treatment planning system stores machine scanning parameters in order to optimize a treatment plan for dose rate (e.g., to maximize the dose rate for normal tissue). The machine scanning parameters can include both a dose component and a timing component. The dose rate can be maximized based on the timing component and a desired dose.

Figure 5B:
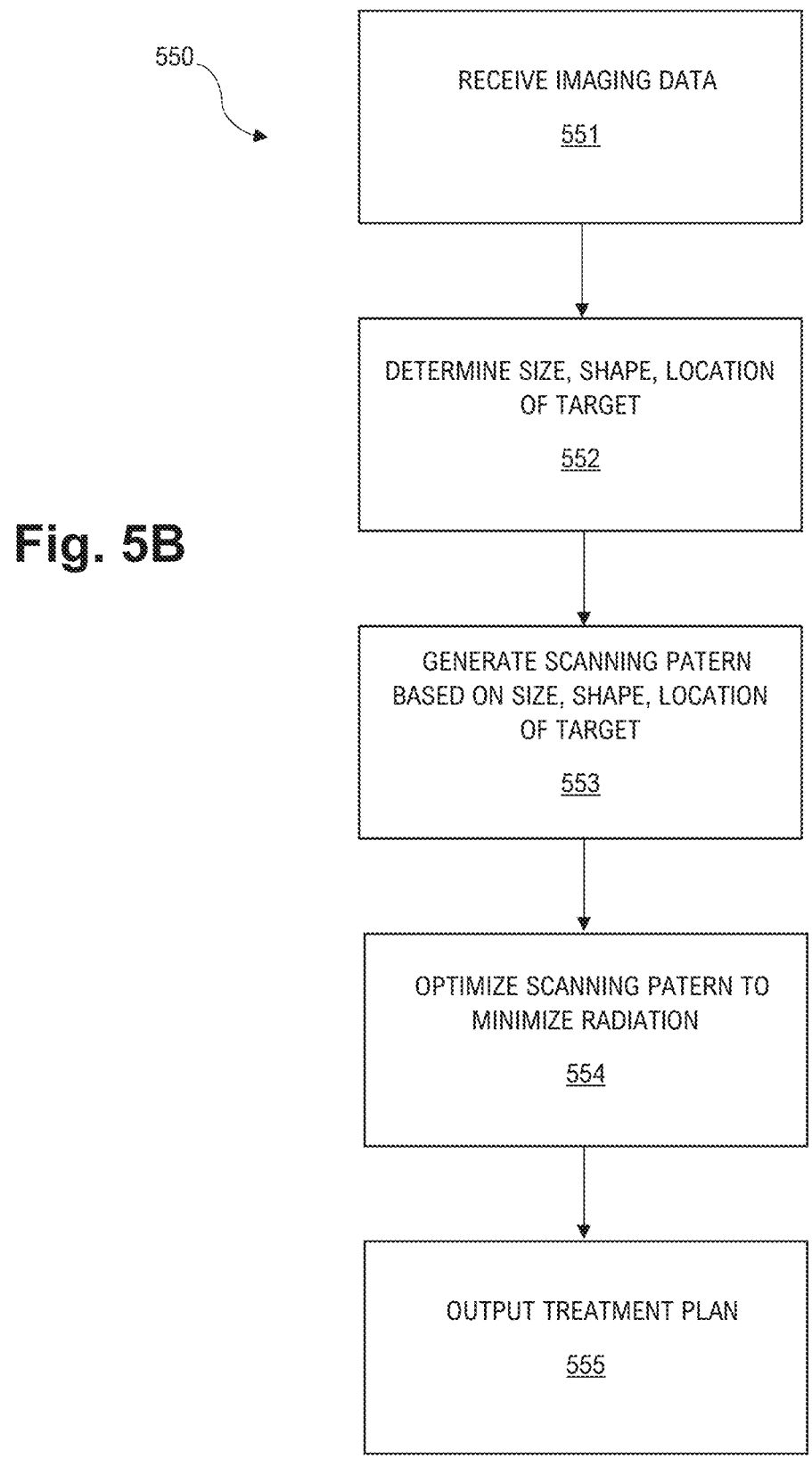
FIG. 5B is a flow-chart depicting an exemplary sequence of computer controlled steps for automatically creating an optimized proton therapy treatment plan and scanning pattern to minimize the amount of radiation received by healthy tissue according to embodiments of the present invention.

With regard to FIG. 5B, an exemplary sequence of computer implemented steps 550 for automatically generating a proton therapy treatment plan is depicted according to embodiments of the present invention. The procedure 550 produces a proton treatment plan that is optimized to minimize a total dose received by health tissue of a patient while treating a target volume.

At step 551, imaging data of a target volume is received. The image data can originate from computer memory or from a scan of a target volume of a patient.

At step 552, the size, shape, and/or location of the target volume is determined based on computations involving the imaging data.

At step 553, the scanning pattern is generated based on the size, shape, and/or location of the target volume.

At step 554, the scanning pattern is optimized to minimize an amount of radiation received by health tissue of the patient. The scanning pattern may comprise a substantially spiral-shaped scanning pattern.

At step 555, a proton therapy treatment plan is output comprising the scanning pattern. The proton therapy treatment plan is operable to instruct a proton therapy treatment system to perform proton therapy treatment according to the scanning pattern.

Figure 6A:
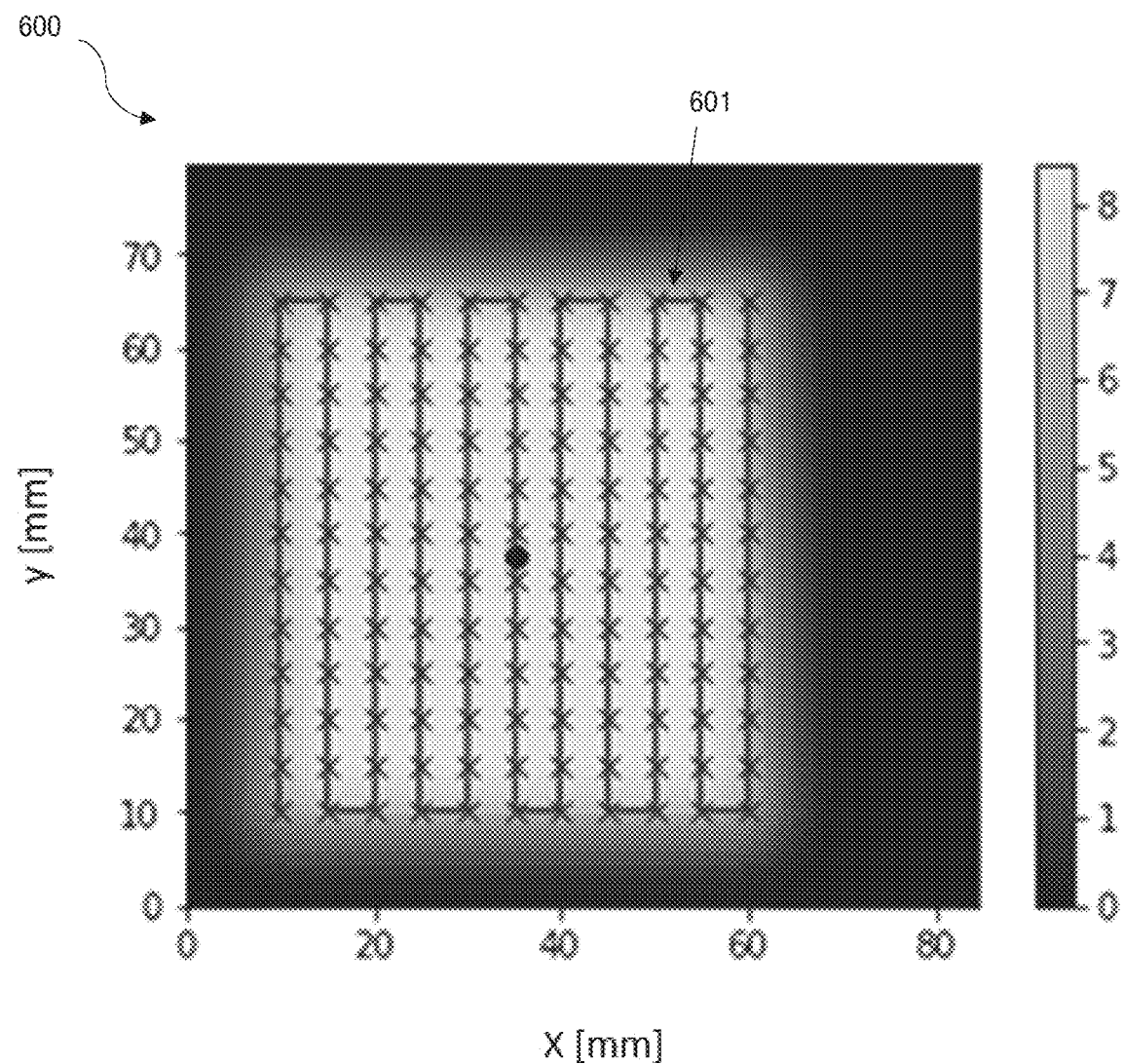
FIG. 6A is a diagram of an exemplary proton therapy treatment plan and standard scanning pattern.

With regard to FIG. 6A, an exemplary proton therapy treatment plan 600 including a standard scanning pattern 601 applied to a target volume (e.g., a tumor or organ) which is surrounded by normal tissue for proton therapy treatment is depicted. This treatment plan 600 is not optimized for PBS FLASH delivery because the treatment plan 600 is generated using limited optimization based on the total dose received by the patient. The treatment plan 600 depicted in FIG. 6A may not use the full system/machine capability (e.g., dose rate) because the treatment plan 600 is generated to optimize total dose and does not consider the dose rate. Therefore, the standard scanning patterns 601 are limited to a lower dose rate than what is achievable using the proton therapy system, which is especially disadvantageous in the context of PBS FLASH delivery. As depicted in FIG. 6A, the treatment plan is further constrained because the treatment spots (represented by an 'X' on the scanning pattern) must be aligned to a grid-shaped pattern, and treatment spots cannot be placed between the lines of the grid-shaped pattern. A more efficient approach for FLASH treatment planning uses novel scanning patterns optimized in accordance with the present invention to achieve higher dose rates, as depicted in FIG. 7A.

Figure 6B:
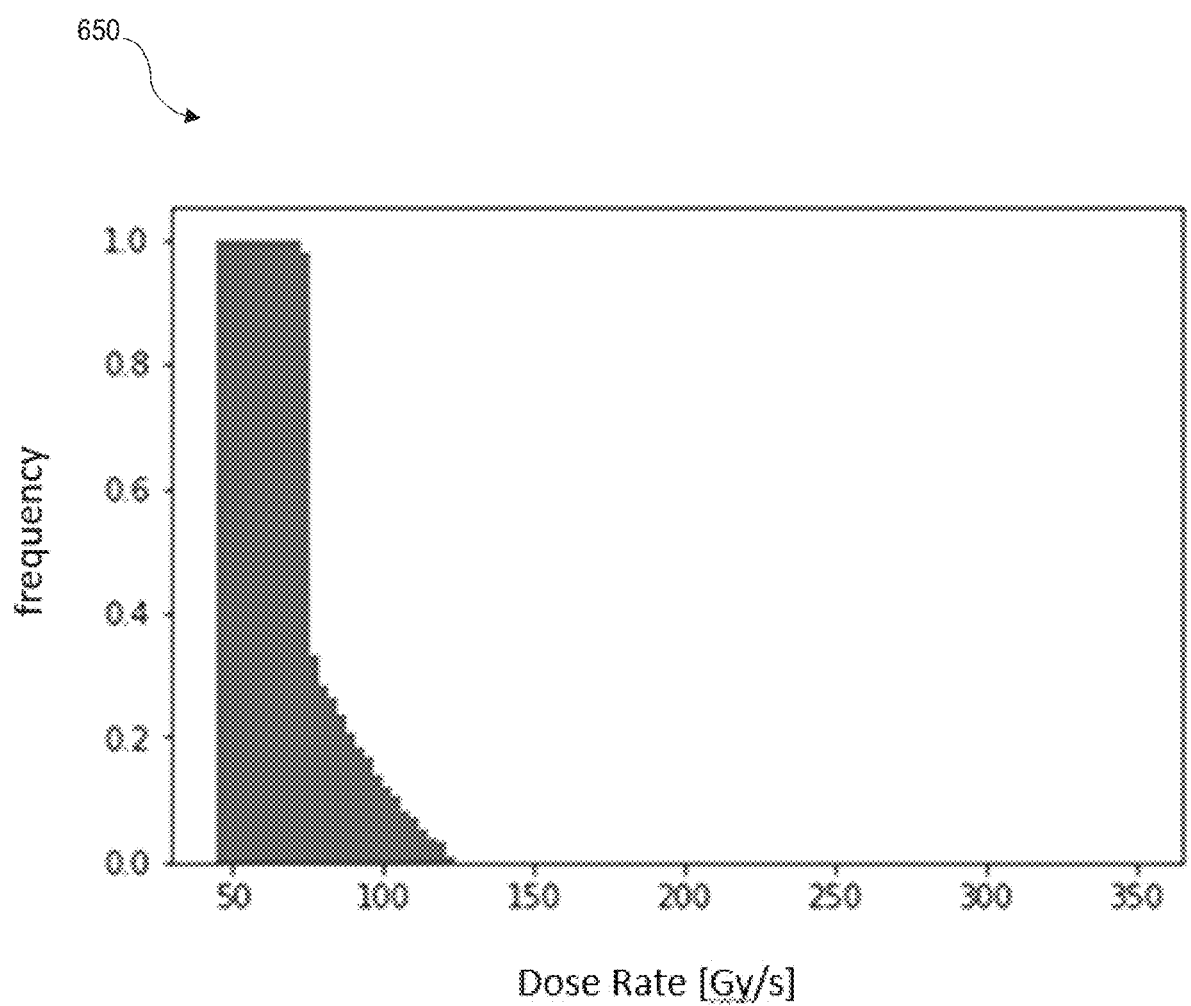
FIG. 6B is a dose rate histogram of the exemplary proton therapy treatment plan and standard scanning pattern depicted in FIG. 6A.

FIG. 6B depicts a dose rate histogram 650 corresponding to the exemplary proton therapy treatment plan 600 including the standard scanning pattern 601 applied to a target volume depicted in FIG. 6A. The dose rate achieved using the standard scanning pattern 601 is relatively low (120 Gy/s) compared to the dose rate achieved using scanning patterns of proton therapy treatment plans optimized according to embodiments of the present invention.

Figure 7A:
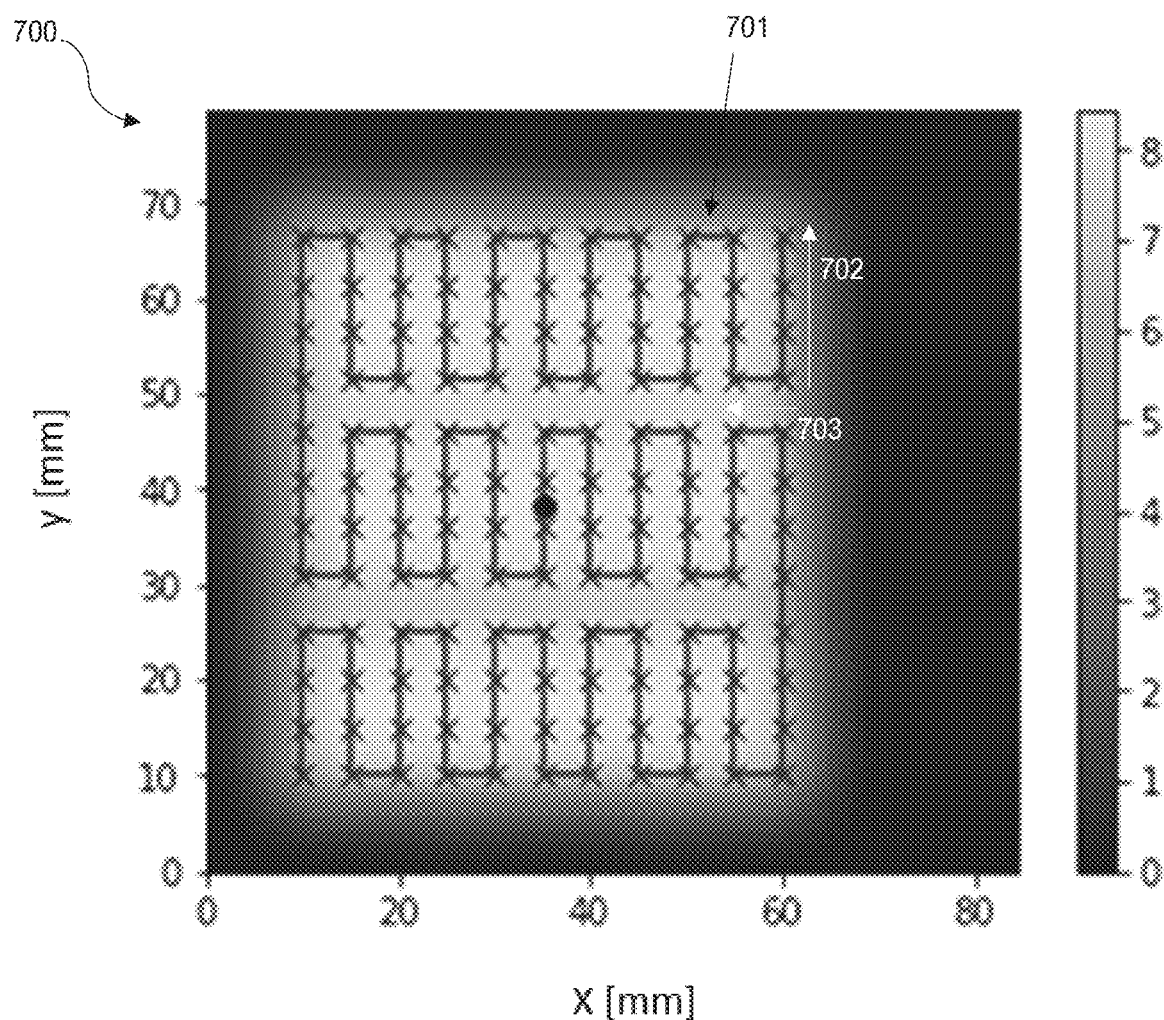
FIG. 7A is a diagram of an exemplary proton therapy treatment plan and optimized scanning pattern for increasing or maximizing a dose rate applied to a target volume depicted according to embodiments of the present invention.

With regard to FIG. 7A, an exemplary optimized proton therapy treatment plan 700 is shown in accordance with the present invention and suitable for PBS FLASH delivery. Treatment plan 700 includes optimized scanning pattern 701 that causes a proton therapy system (e.g., a gantry) to scan a beam (e.g., a pencil beam) faster in one direction compared to another direction to advantageously achieve a relatively high dose rate. For example, in the example depicted in FIG. 7A, the beam applied using optimized scanning pattern 701 is scanned faster in the vertical direction 702 of rectangular subfield 703 than the horizontal direction 704 to optimize the dose rate applied by the proton therapy system. According to some embodiments, the size/area of the subfield 703 is determined based on a desired dose rate and/or a given nozzle current. As depicted in FIG. 7A, the scanning pattern and the spots applied align to a grid shaped pattern. However, it is appreciated that the scanning pattern and the spots thereof can be freely placed without conforming to a grid-shaped pattern, as depicted in FIG. 8.

Figure 7B:
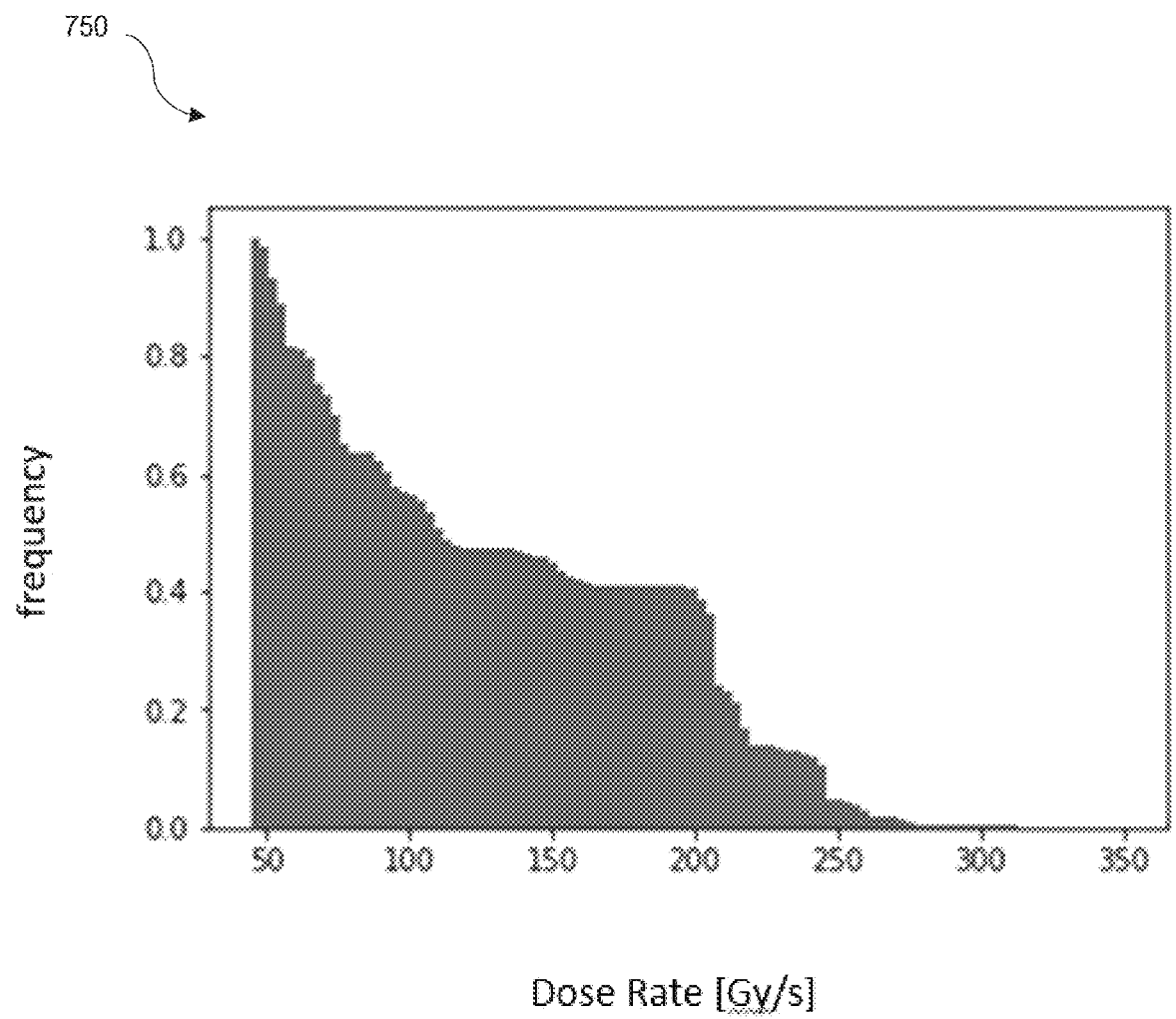
FIG. 7B is a dose rate histogram of the exemplary proton therapy treatment plan depicted in FIG. 7A in accordance with embodiments of the present invention.

FIG. 7B depicts a dose rate histogram 750 corresponding to the exemplary proton therapy treatment plan 700 including the standard scanning pattern 701 applied to a target volume depicted in FIG. 7A. The dose rate achieved using the standard scanning pattern 701 is relatively high (310 Gy/s) compared to the dose rate achieved using standard scanning patterns and is suitable for PBS FLASH delivery.

Figure 8:
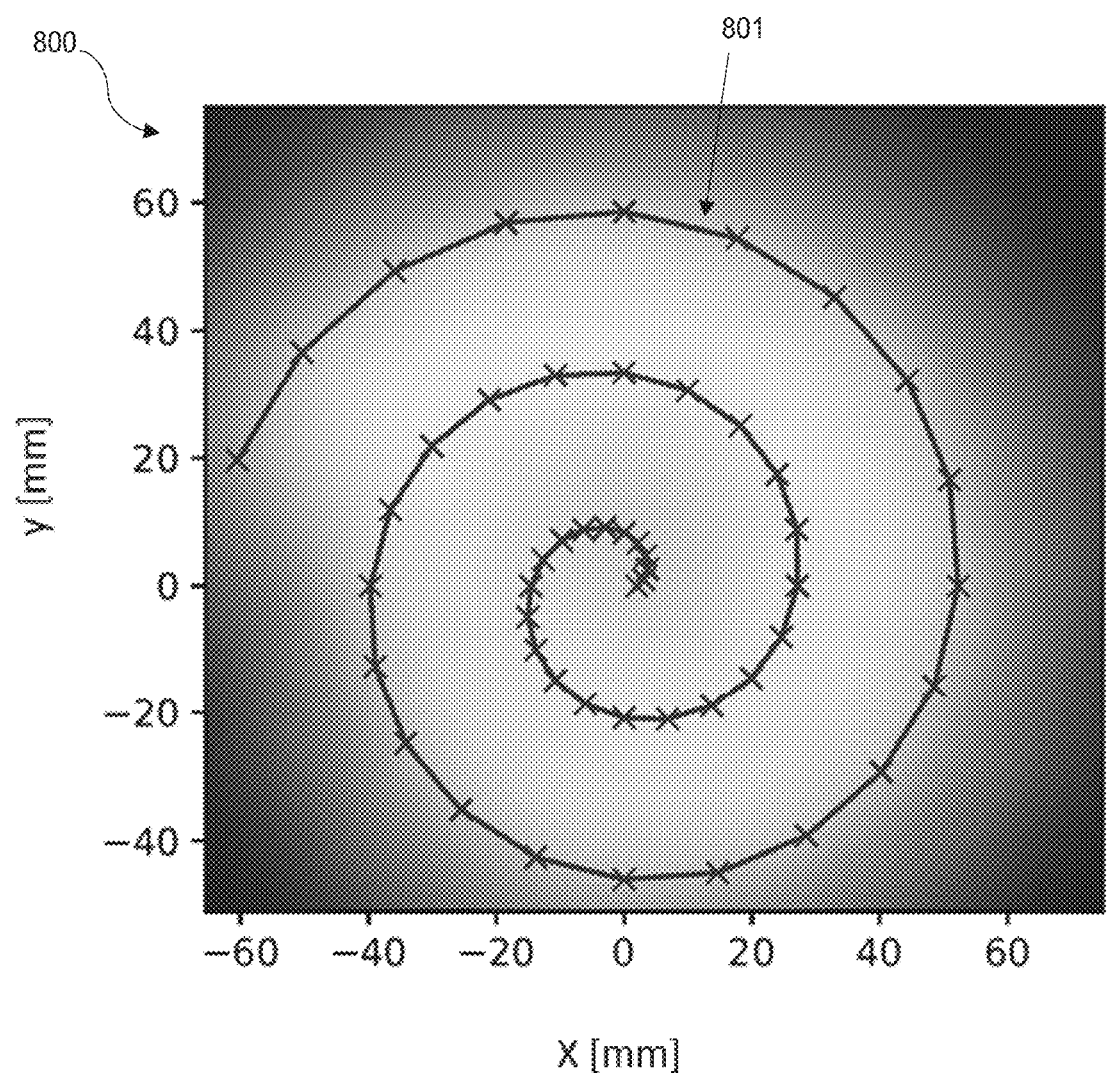
FIG. 8 is a diagram of an exemplary proton therapy treatment plan and optimized scanning pattern for minimizing the amount of radiation received by healthy tissue depicted according to embodiments of the present invention.

With regard to FIG. 8, an exemplary optimized proton therapy treatment plan 800 is shown including scanning pattern 801 that causes a proton therapy system (e.g., a gantry) to scan a beam (e.g., a pencil beam) to apply a desired dose rate and minimize the amount of irradiation received by healthy tissue (e.g., healthy tissue voxels). For example, in the example depicted in FIG. 8, the beam is scanned in a spiral-shaped pattern to minimize the amount of dose received by health tissue. According to some embodiments, the size/area of the spiral-shaped pattern is determined based on a desired dose rate, the size/shape of the target volume, and/or a given nozzle current. As depicted in FIG. 8, the scanning pattern and the spots applied are freely placed without conforming to a grid-shaped pattern. In this way, the scanning pattern can better conform to the size/shape of the target volume and can minimize the amount of radiation received by healthy tissue.

Embodiments of the present invention, an improved approach to FLASH treatment planning that can maximize the dose rate for different target sizes, shapes, and locations including relatively large targets, are thus described. While the present invention has been described in particular embodiments, it should be appreciated that the present invention should not be construed as limited by such embodiments, but rather construed according to the following claims.

What is claimed is:

1. A system comprising:
 a gantry including a nozzle configured to emit a controllable beam;
 a radiation therapy treatment system configured to control the gantry according to a treatment plan; and
 a treatment planning system including
  a memory configured to store image data and the treatment plan; and
  a processor configured to perform a method of generating the treatment plan, the method including
   receiving imaging data of a target volume,
   dividing the imaging data of the target volume into a scanning pattern including a plurality of subfields having a first beam path scanning direction and a second beam path scanning direction to achieve a desired dose within the target volume and to achieve a maximum dose rate within a volume at risk, wherein the plurality of subfields have first beam path scan lengths of consecutive spot locations in the first beam path scan direction and second beam path scan lengths of consecutive spot locations in the second beam path scan direction, wherein a plurality of the first beam path scan lengths of consecutive spot locations and a plurality of the second beam path scan lengths of consecutive spot locations are less than a longest length of consecutive spot locations in the scanning pattern, and
   outputting the treatment plan including the scanning pattern, wherein the treatment plan is operable to instruct the radiation therapy treatment system to perform a radiation therapy treatment on the target volume according to the scanning pattern including independently scanning each subfield in the first beam path scanning direction at a faster scanning rate, and scanning in the second beam path scanning direction at a slower scanning rate.

2. The system as recited in claim 1, wherein the radiation therapy treatment system is configured to perform a method for radiation therapy treatment on the target volume according to the scanning pattern, the method for radiation therapy treatment including scanning each subfield independently in the first beam path scanning direction at a faster scanning rate, and scanning in the second beam path scanning direction at a slower scanning rate.

3. The system as recited in claim 1, wherein the method further comprises receiving the maximum dose rate as input.

4. The system as recited in claim 1, wherein the method further comprises determining the maximum dose rate according to a machine specific capability limitation of the radiation therapy treatment system.

5. The system as recited in claim 1, wherein the dividing the imaging data of the target volume into a scanning pattern including a plurality of subfields is performed based on at least one of a size of the target volume, a shape of the target volume, or a location of the target volume.

6. A method of radiation therapy treatment comprising:
 receiving imaging data of a target volume;
 dividing the imaging data of the target volume into a scanning pattern including a plurality of subfields having a first beam path scanning direction and a second beam path scanning direction to achieve a desired dose within the target volume and to achieve a maximum dose rate within a volume at risk, wherein the plurality of subfields have first beam path scan lengths of consecutive spot locations in the first beam path scan direction mid second beam path scan lengths of consecutive spot locations in the second beam path san direction, and wherein a plurality of the first beam path scan lengths of consecutive spot locations and a plurality of the second beam path scan lengths of consecutive spot locations are less than a longest length of consecutive spot locations in the scanning pattern; and outputting a radiation therapy treatment plan operable to instruct a radiation therapy treatment system to perform a radiation therapy treatment according to the scanning pattern including independently scanning each subfield in the first beam path scanning direction at a faster scanning rate, and scanning in the second beam path scanning direction at a slower scanning rate.

7. The method as recited in claim 6, further comprising performing the radiation therapy treatment using the radiation therapy treatment system according to the radiation therapy treatment plan.

8. The method as recited in claim 6, further comprising receiving the maximum dose rate as an input.

9. The method as recited in claim 6, further comprising; determining the maximum dose rate according to a machine specific upper limit dose rate associated with the radiation therapy treatment system.

10. The method as recited in claim 6, wherein the dividing the imaging data of the target volume into a scanning pattern including a plurality of subfields is performed based on at least one of a size of the target volume, a shape of the target volume, or a location of the target volume.

11. The method as recited in claim 6, wherein the scanning pattern is aligned to a grid-shaped pattern.

12. The method as recited in claim 6, wherein the scanning pattern is not aligned to a grid-shaped pattern.

13. The method as recited in claim 6, wherein the radiation therapy treatment plan is operable to instruct the radiation therapy treatment system to perform a FLASH proton therapy treatment including delivering a proton therapy treatment in a single treatment with a dose rate of 4 grays (Gy) or more in less than one second.

14. The method as recited in claim 6, wherein the radiation therapy treatment system is configured for pencil beam scanning.

15. The system as recited in claim 1, wherein
the plurality of subfields include a plurality of rectangular subfields; and
the first beam path scanning direction includes a long dimension of the rectangular subfields and the second beam path scanning direction includes a short dimension of the rectangular subfields.

16. The system as recited in claim 1, wherein the dividing divides the image data of the target volume into the scanning pattern to achieve a minimum dose within the volume at risk.

17. The system as recited in claim 1, wherein:
the radiation therapy treatment system includes a proton therapy treatment system;
the radiation therapy treatment includes a proton therapy treatment; and
the treatment plan includes a proton therapy treatment plan.

18. The system as recited in claim 17, wherein the proton therapy treatment plan comprises a FLASH proton therapy treatment plan delivering the proton therapy treatment in a single treatment with a dose rate of 4 grays (Gy) or more in less than one second.

19. The system as recited in claim 1, wherein the radiation therapy treatment system is configured for pencil beam scanning.

* * * * *